(12) United States Patent
Sitasawad et al.

(10) Patent No.: US 8,519,163 B2
(45) Date of Patent: Aug. 27, 2013

(54) **ANTI-TUMOR ACTIVITY OF AECHL-1, NOVEL TRITERPENOID ISOLATED FROM *AILANTHUS EXCELSA* IN VITRO AND IN VIVO**

(75) Inventors: Sandhya Sitasawad, Pune (IN); Manish Lavhale, Vadodara (IN); Santosh Kumar, Pune (IN); Shrihari Mishra, Vadodara (IN)

(73) Assignees: National Centre for Cell Science, Pune (IN); Department of Biotechnology, New Delhi (IN)

( * ) Notice: Subject to any disclaimer, the term of this patent is extended or adjusted under 35 U.S.C. 154(b) by 9 days.

(21) Appl. No.: 12/742,139

(22) PCT Filed: Dec. 2, 2008

(86) PCT No.: PCT/IN2008/000795
§ 371 (c)(1),
(2), (4) Date: Aug. 25, 2010

(87) PCT Pub. No.: WO2010/035277
PCT Pub. Date: Apr. 1, 2010

(65) Prior Publication Data
US 2010/0311987 A1    Dec. 9, 2010

(30) Foreign Application Priority Data
Sep. 26, 2008    (IN) .............................. 2261/DEL/08

(51) Int. Cl.
*C07D 493/00* (2006.01)

(52) U.S. Cl.
USPC .......................................................... 549/278

(58) Field of Classification Search
USPC ......................................................... 549/278
See application file for complete search history.

(56) References Cited

PUBLICATIONS

Lavhale, Manish S. et al, (2009), "A Novel Triterpenoid Isolated from the Root Bark of *Ailanthus excelsa* Roxb (Tree of Heaven), AECHL-1 as a Potential Anti-Cancer Agent)", *PLoS ONE*, 4(4): e5365 doi:10.1371/journal.pone.0005365.

*Primary Examiner* — Nizal Chandrakumar
(74) *Attorney, Agent, or Firm* — Venable LLP; Nancy J. Axelrod; Keith G. Haddaway

(57) ABSTRACT

A novel chemical moiety triterpenoid AECHL-1 isolated from root bark of *Ailanthus excelsa* having the structure:

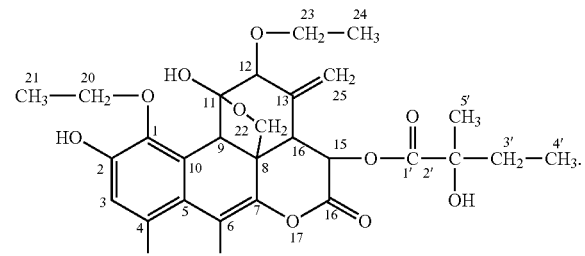

1 Claim, 12 Drawing Sheets

Fig. 3 (MDA-MB-231)

Fig. 4 (MCF-7)

Fig. 8
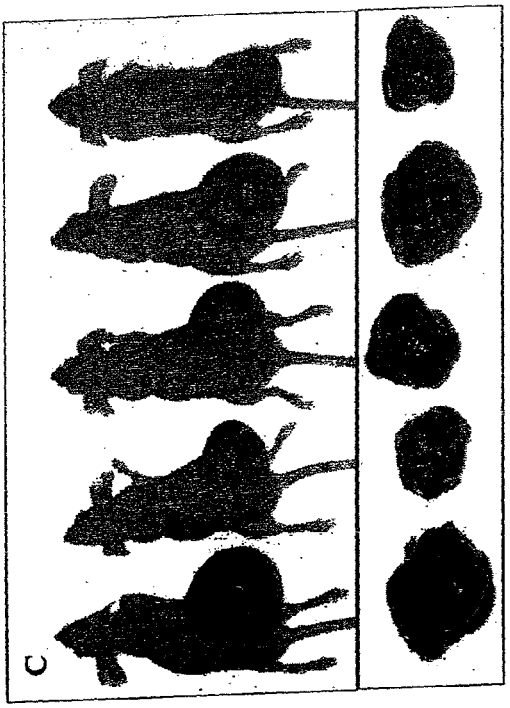
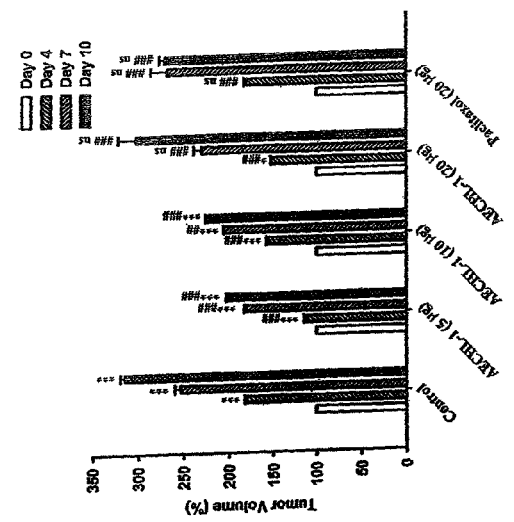
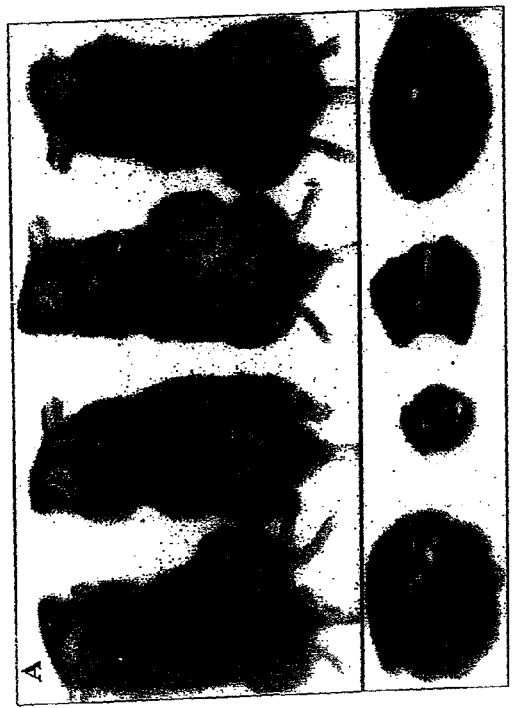
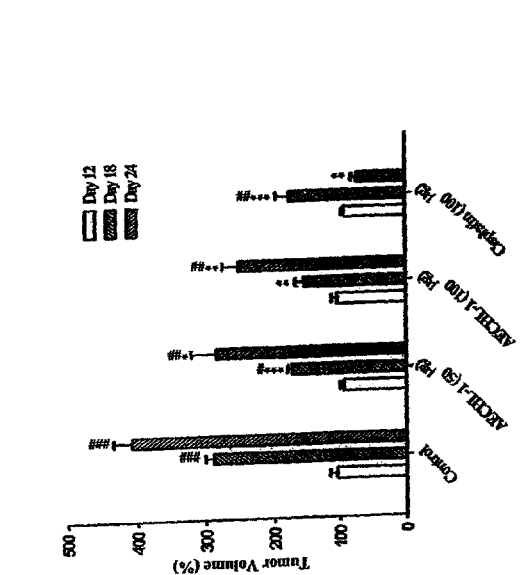

ANTI-TUMOR ACTIVITY OF AECHL-1, NOVEL TRITERPENOID ISOLATED FROM *AILANTHUS EXCELSA* IN VITRO AND IN VIVO

FIELD OF INVENTION

This invention relates to a novel triterpenoid AECHIL-1, isolated from *Ailanthus excelsa* having anti tumor activity both in vitro and in vivo.

BACKGROUND OF INVENTION

The existing state of art in the treatment of cancer includes Chemotherapy that involves the administration of different chemical compounds either alone or in combination of more than one such compounds in treatment of cancer either inhibiting growth or killing cancer cells. The most commonly employed chemically modified compounds like Paclitaxel from Pacific yew tree, Etoposide from Podophylum tree, and Vincristine from Vinca plant, while other compounds like Cisplatin, Mitomycin, Daunarubicin, Adriamycin, Interferrons are also employed. Radiotherapy is another type of therapy involved to shrink and destroy tumors by damaging the genetic material, making further growth and division impossible for the cells.

Cryotherapy is the creation of extreme cold environment using liquid nitrogen (or argon gas) which destroy abnormal tissue and used to treat external tumors, such as those on the skin. Immunotherapy is the utilization of toxin tagged with monoclonal antibodies in the treatment of cancer.

The most important drawback of all the above therapies is that, these harm healthy cells and damage different organs like heart, lungs, nerves, kidneys, or reproductive organs ultimate causing death. Other side effects include anemia, loss of appetite, hemorrhage, fatigue, flu-like symptoms, fluid retention, hair loss, infertility, mouth and throat changes, nausea and vomiting, pain, sexual changes, skin and nail changes, eye changes, urinary, kidney, and bladder changes.

Plants have a long history of use in the treatment of cancer. Plant-derived compounds have been an important source of several clinically useful anti-cancer agents. Numerous plant-derived compounds including vinblastine, vincristine, camptothecin derivatives, topotecan and irinotecan, etoposide, derived from epipodophyllotoxin, and paclitaxel (taxol) are used in cancer chemotherapy but most exhibit cell toxicity and can induce genotoxic, carcinogenic and teratogenic effects in non-tumor cells. These side effects limit the use of chemotherapeutic agents despite their high efficacy in treating target malignant cells. Therefore, the search for alternative drugs that are both effective and non-toxic in the treatment of cancers is an important research line.

Root bark of *Ailanthus excelsa* Roxb (Tree of Heaven), a tree, indigenous to central and southern India, belonging to family Simaroubaceae is widely used in Ayurveda and evidence based phytotherapy. Other species from this family are well known for their anti-cancer activities. Chemical constituents of *A. excelsa* include triterpenes and alkaloids. The aim of the present study was to evaluate the in vitro cytotoxic and in vivo anti-tumor effect of a new triterpenoid moiety (AECHL-1) isolated from the root bark of *Ailanthus excelsa*.

AECHL-1 obtained from root bark of *Ailanthus excelsa* tree could overcome some of these drawbacks like hair loss, cardiotoxicity, hepatotoxicity, nephrotoxicity, at the effective dose level. Compared to other agents used in the treatment of tumors, AECHL-1 is a cost effective, being easily available from a plant as its source and is non toxic to normal cells unlike most of the anti-cancer agents.

The molecule of the present invention was isolated from the root bark of the tree *Ailanthus excelsa*, and has been shown to possess cytotoxic effect in various cancer cells. The anti-tumor effect of a molecule (designated AECHL-1) was very broad, because it blocked the growth of four tumor cell lines with distinct origins and of different p53 status (B16 mouse melanoma, PC3 human prostate cancer, MCF-7 and MDA-231 human breast cancer) and showed less cytotoxicity in normal human embryonic kidney cells HEK 293. In the tumors of different origin i.e. B16F10 and MCF-7 grown in C57 and nude mice respectively, AECHL-1 showed significant reduction in tumor volume. The two clinically useful agents, cisplatin and paclitaxel were used as reference standards for both in vitro and in vivo studies, where effects of AECHL-1 were found to be comparable with paclitaxel and cisplatin.

AECHL-1 inhibited cell viability/proliferation in a concentration-dependent manner. It showed inhibition of PC3 cell proliferation by arresting cell cycle in G2/M phase. In MDA-MB 231 cells, it arrested the growth in S-G2/M phase, while it showed growth arrest at G0/G1 phase in B16F10 cells. In MCF-7 cells it arrested the growth in S-G2/M phase.

It is the first time that the molecule is isolated and characterized from the *Ailanthus excelsa* and was also investigated for the reported properties.

Therefore no information on the knowledge of the present invention at national as well as international levels is available.

OBJECT OF INVENTION

The main object of the present invention is to develop new triterpenoid AECHL-1 isolated from the root bark of *Ailanthus excelsa* Roxb having anti cancer property.

Other object is to evaluate the in vitro and in vivo anti cancer properties.

Another object is to develop a new triterpenoid molecule that exhibit remarkable activity in treatment of various forms of tumors with specificity in different cancers in clouding mouse melanoma and human breast and prostate cancer.

Yet another object is to develop a new triterpenoid molecule having anti cancer activity and to study the mechanism of death effect in several model systems.

STATEMENT OF INVENTION

A novel chemical moiety triterpenoid AECHL-1 isolated from root bark of *Ailanthus excelsa* having anti-cancer properties exhibiting remarkable activity in treatment of various forms of tumors with specificity wherein it blocks the growth of four tumor cell lines with distinct origins and of different p53 status (B16F10 mouse melanoma, PC3 human prostate cancer, MCF-7 and MDA-MB-231 human breast cancer), having following characteristic IR, NMR and mass spectra IR (KBr): 3425, 3419 (hydroxyl group), 2972, 2966, 2923, 2873 (alkyl C—H stretch), 1733 (δ lactone), 1718 (Bi acetyl), 1680 (C=O conjugation with alkene), 1652 (—C=C stretching), 1600 (aromatic), 1492, 1454, 1394 (methyl stretching), 1222 (δ lactone), 1184, 1110, 1051, 1031 (acetals), 1018 nm (alkanes). $^1$H-NMR (DMSO, 400 Hz) δ: 0.95 (3H, t, 4'-CH$_3$), δ: 1.15 (3H, d, H-24), δ: 1.235 (3H, d, 5'-CH$_3$), δ: 1.5 (2H, ddd, 5'-CH$_2$), δ: 1.73 (3H, ddd, H-21), δ: 1.83 (1H, s, H-9), δ: 1.87 (1H, s, H-14), δ: 1.9 (2H, s, H-18), δ: 2.16 (3H, s, H-18), δ: 2.3 (3H, d, H-19) δ: 2.71 (2H, s, H-20), δ: 3.45 (2H, dd, H-23), δ: 3.65 (2H, d, H-22), δ: 3.95 (1H, t, H-12), δ: 4.05 (2H, s, H-22), δ: 5.30 (1H, s, H-15), δ: 5.46 (1H, s, OH-2), δ: 5.73 (1H, d, OH-2'), δ: 6.89 (1H, s H-3), δ: 8.82 (1H, s, OH-11). Chemical shifts are given in ppm on the δ-scale, s=singlet, d=doublet, t=triplet. The mass spectra showing the following principal peaks: m/z: 1068 due to dimer formation. The actual [M$^+$] was considered to be 543.8, 463.3 [M-C$_4$H$_1$O$_2$], 461.4 [M-C$_4$H$_2$O$_2$], 459.4 [M-C$_4$H$_4$O$_2$], 361.2 [M-C$_9$H$_{11}$O$_4$] is a solid, mp. 248-250° C. possessed a molecular formula of C$_{29}$H$_{36}$O$_{10}$ as indicated by EI and ES mass spectra.

DESCRIPTION OF THE ACCOMPANYING DRAWINGS

FIG. 1 shows the effect of various agents on B16F10 cells. FIG. 1A shows the % cell viability at the indicated times after treatment with the indicated amounts of cisplatin. FIG. 1B shows the % cell viability at the indicated times after treatment with the indicated amounts of paclitaxel. FIG. 1C shows the % cell viability at the indicated times after treatment with the indicated amounts of AECHL-1. FIG. 1D shows the % survival rate at the indicated times after treatment with the indicated amounts of AECHL-1.

FIG. 2 shows the effect of various agents on PC3 cells. FIGS. 2A, 2B and 2C show, respectively, the % cell viability at the indicated times after treatment with the indicated amounts of cisplatin, paclitaxel or AECHL-1. FIGS. 2D, 2E and 2F show, respectively, the % survival rate at the indicated times after treatment with the indicated amounts of cisplatin, paclitaxel or AECHL-1.

FIG. 3 shows the effect of various agents on MDA-MB-231cells. FIGS. 3A, 3B and 3C show, respectively, the % cell viability at the indicated times after treatment with the indicated amounts of cisplatin, paclitaxel or AECHL-1. FIGS. 3D, 3E and 3F show, respectively, the % survival rate at the indicated times after treatment with the indicated amounts of cisplatin, paclitaxel or AECHL-1.

FIG. 4 shows the effect of various agents on MCF-7 cells. FIGS. 4A, 4B and 4C show, respectively, the % cell viability at the indicated times after treatment with the indicated amounts of cisplatin, paclitaxel or AECHL-1. FIGS. 4D, 4E and 4F show, respectively, the % survival rate at the indicated times after treatment with the indicated amounts of cisplatin, paclitaxel or AECHL-1.

FIGS. 5A and 5B show that after 12, 24 and 48 h of treatment, the percent viability of the tumor cells was significantly inhibited by AECHL-1 in a concentration and time dependent manner in all cell lines as indicated by MTT. Both figures show the % cell viability (or % survival rate) as a function of concentration of AECHL-1; different cell lines are shown as indicated in the two figures. The inhibition rate increased in a concentration and time dependent manner, and maximum effect was observed at higher concentration after 48 h of treatment with AECHL-1 in the cell lines as MCF-7>B16F10>PC3>MDA-MB-231>HEK 293 (FIG. 5A). Significantly, the inhibitory effect of AECHL-1 at 10 µM was stronger than that of Paclitaxel, or Cisplatin in MCF-7 cells treated for 48 h (FIG. 5B) suggesting that AECHL-1 is very potent.

FIG. 6 illustrates the relative cell growth arrest of different cells at different concentrations is evident visually in phase contrast images of random fields of cells.

FIG. 7 tested whether AECHL-1 treatment affected the cellular microtubule network. MCF-7 cells were treated with various concentrations of paclitaxel (1-20 µM) (FIG. 7A) and AECHL-1 (2-40 µM) (FIG. 7B). After 24 h of incubation, the p53 translocation in the nucleus and microtubule network was visualized by confocal microscopy. AECHL-1 treatment resulted in translocation of the p53 into the nucleus. The microtubule network in control cells exhibited normal arrangement and organization. Treatment with paclitaxel resulted in microtubule polymerization with an increase in the density of cellular microtubules and formation of long thick microtubule bundles surrounding the nucleus. AECHL-1 treatment resulted in findings similar to those of paclitaxel-induced microtubule changes, such as thickening and increased density of microtubules.

FIG. 8 shows the effect of AECHL-1 on primary tumor volume in allogaft and xenograft. (A) Photographs of C57BL/6 mice showing 4-week-old allograft tumor growth by B16F10 cells; below, excised tumors with respective mice; (B) Tumor volume was determined at timed intervals as described in the application. Tumor volume of experimental animals after treatment with 50, 100 µg AECHL-1 and 100 µg cisplatin was compared with the tumor volume of control animals; (C) Photographs of athymic nude mice showing 4-week-old xenograft tumor growth by MCF-7 cells; below, excised tumors with respective mice; (D) Tumor volume of experimental animals after treatment with 5, 10 µg AECHL-1 and 20 µg paclitaxel was compared with the tumor volume of control animals. Results represent the mean±SE of six starting animals in each group. Significant differences between *Intra group at each time point are represented as: ns p>0.05, *p<0.05 P<0.01, *P<0.001 and #Inter group at different doses are represented as ns P>0.05, #<0.05, ##P<0.01, ###P<0.001.

FIG. 9A shows in control group and in mice treated with 100 µg AECHL-1 and Cis-platin, a reduction in body weight (including tumor) was observed. Whereas the body weight was not reduced in case of mice treated with 50 µg AECHL-1.

FIG. 9B shows Treatment with 50 and 100 µg AECHL-1 and cis-platin showed significant reduction in tumor weight to body weight ratio after 12 days treatment (p<0.01) compared with control group. Compared to 100 µg AECHL-1, the effect was more in 50 µg AECHL-1. Compared with AECHL-1 and control groups cis-platin treated group showed significant reduction in ratio.

Figure 10:
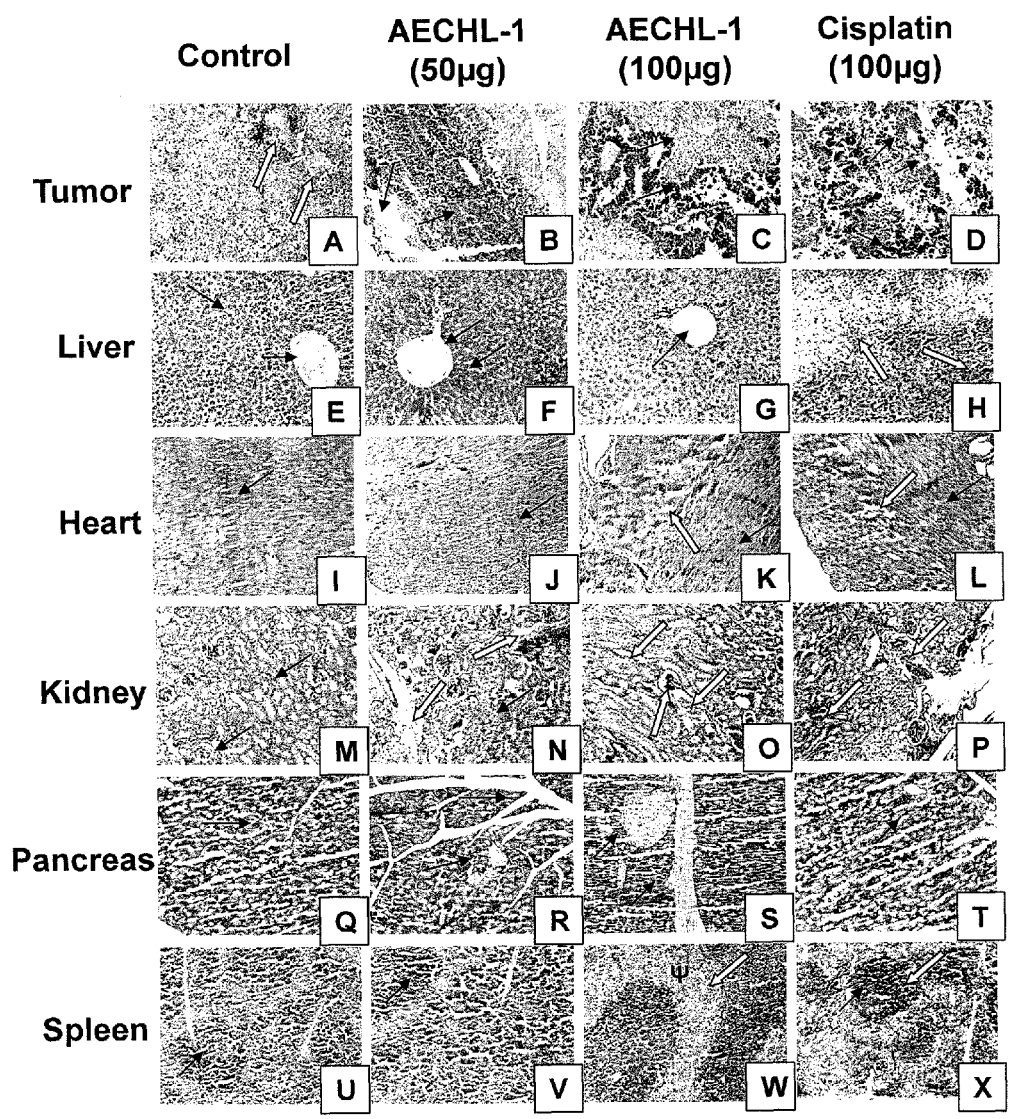
FIG. 10A shows blood vessels were found to be well developed.
FIG. 10B shows vessels perfused as indicated by the presence of erythrocytes. Therefore necrosis in these areas did not seem to be the result of lack of vascularization.

FIG. 10C demonstrates treatment of tumors with 100 µg AECHL-1 showed increase in necrotic nuclei through out the tumor area, with disappearance of neovasulization and hemorrhagic areas and therefore reduced the chances of angiogenesis and metastasis. Tumor cell density was found to be lower compared to that of 50 µg AECHL-1 and vehicle treated group.

FIG. 10D Cis-platin treated group showed significant increase in necrotic nuclei with decreased tumor cell density.

FIG. 10E-FIG. 10U-X shows Histopathological examination of organs in C57 mice Histological examination of the organs from C57 mice showed following data Liver from control group showed the central vein with portal triads at the periphery of the lobule. Kupffer cells appeared were normal (FIG. 10E). 50 µg AECHL-1 did not affect the normal architect of the liver (FIG. 10F) and 100 µg AECHL-1 retains the normal architect of the liver with hypertrophic cell nucleus (FIG. 10G). In cis-platin treated group, extensive hepatocytes necrosis was seen. The hepatocytes shown with arrow at the right side are dead. This pattern can be seen with a variety of hepatotoxins, where focal hepatocytes necrosis with lymphocytic infiltration occurs. Histopathologically, lesions look like that of Tyzzer's disease characterised by necrosis with varying degrees of inflammation in response to the necrosis. Acute hepatic lesions consist of necrotic foci surrounded by minimal, primarily neutrophilic, inflammation (FIG. 10H).

Heart from control group showed parallel fibers with prominent centrally placed nuclei indicating individual cells (FIG. 10I). Treatment with 50 µg AECHL-1 did not show any necrosis of myocardial fibers (FIG. 10J). Treatment with 100 µg AECHL-1 showed extensive myocardial fiber necrosis with contraction bands and loss of nuclei. The fragmentation and smudging of the muscle fibers occur which is characteristic of coagulative necrosis (FIG. 10K). Cis-platin treated mice showed necrosis of myocardial fiber occurs with slight lymphocytic infiltration. Here again the fragmentation and smudging of the muscle fibers characteristic of coagulative necrosis (FIG. 10L).

In control mice kidney showed well demarcated cortex and medulla, and the intact capsule with well formed glomeruli (FIG. 10M). Treatment with 50 µg AECHL-1 showed slight tubular vacuolization and tubular dilation with hemorrhagic areas, normal glomeruli appears at the lower part (FIG. 10N). Treatment with 100 µg AECHL-1 showed tubular vacuolization and tubular dilation with hemorrhagic condition, tubules were dilated with scattered chronic inflammatory cell infiltrates (FIG. 10O). In Cisplatin treated mice lymphocytes were scattered in and around the vessel. The glomerulus is hypercellular and capillary loops were poorly defined which is a type of proliferative glomerulo nephritis. Many neutrophils were seen in the tubules and interstitium i.e. Pyelonephritis (FIG. 10P).

No significant changes occurred in the cellular architecture of pancreas histology (FIG. 10Q-T).

Representative spleen sections from control mice showed different compartments of the white pulp indicated by (*)-periarteriolar lymphatic sheaths; (Θ)-follicles; and (Ψ)-marginal zones. Control and 50 µg AECHL-1 showed normal spleen architect. Note the hyperplasia of the white pulp, especially of the follicles; and marginal zone. Histology showed increased number of granulocytes in the marginal zones (FIG. 10U-X).

Figure 11:
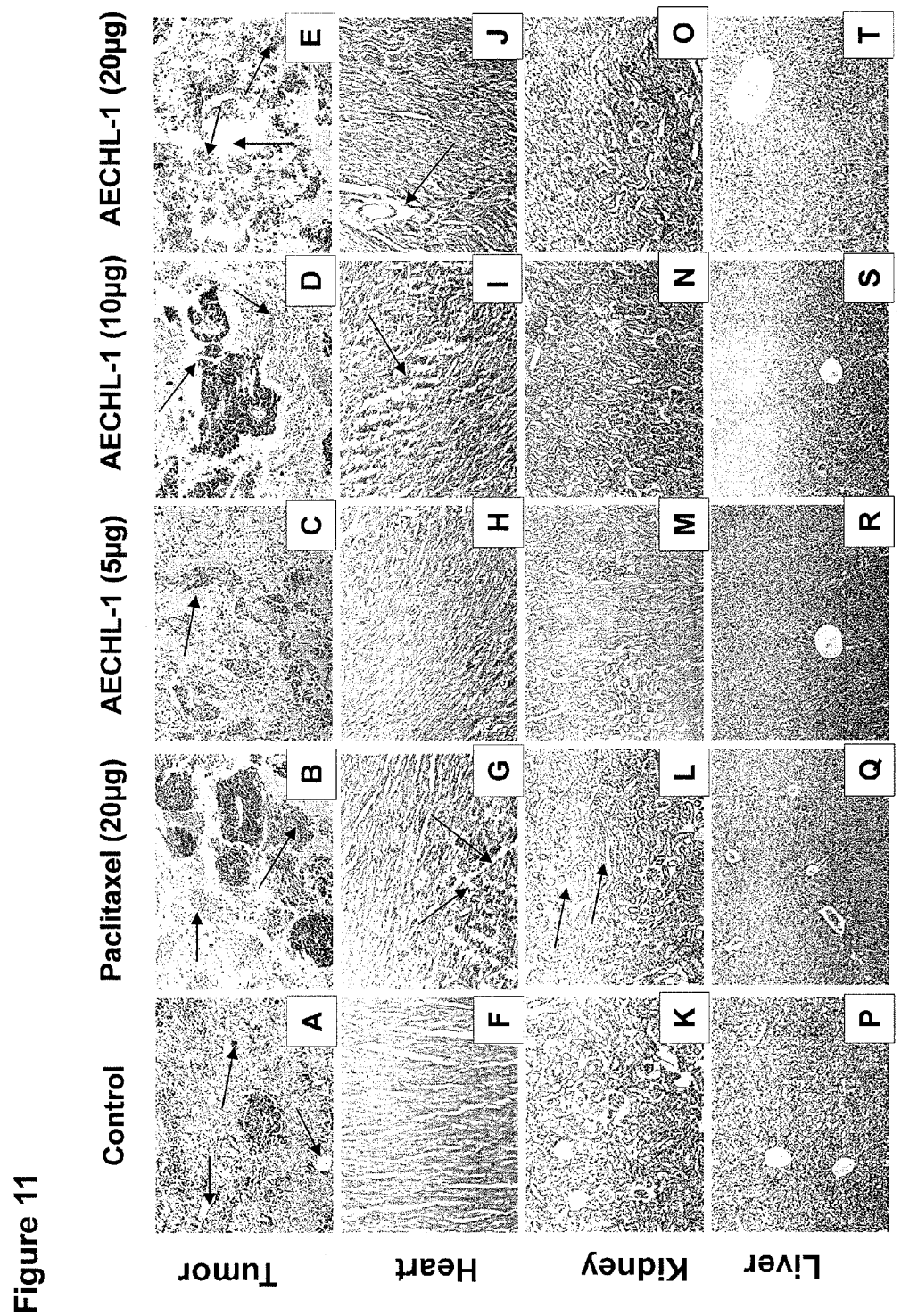

FIG. 11A-11P-T shows Histological examination of tumor tissue in nude mice Histological examination, of tumor in nude mice were similar to that of C57 mice. Tumors from control mice showed pronounced neovascularization throughout the section surrounded with highly dense cells and absence of necrotic cells (FIG. 11A). Treatment with Paclitaxel lowered the tumor cell density with occurrence of many empty spaces and necrotic areas in the section. Paclitaxel did not influence the tumor vascularization with occurrence of blood vessels and hemorrhagic areas (FIG. 11B). AECHL-1 at 5 µg dose showed decreased tumor cell density with lots of empty spaces throughout the tumor area It also showed loss of neovasulization with absence of hemorrhagic areas (FIG. 11C). AECHL-1 at 10 and 20 µg showed similar effects, but was not able to reduce the vascularization with occurrence of hemorrhagic areas. We did not directly assess the functionality of blood vessels in this area, as vessels seemed perfused as indicated by the presence of erythrocytes. Therefore, necrosis in these areas did not seem to be the result of lack of vascularization (FIGS. 11D and E).

Histopathological Examination of the Organs in Nude Mice

Treatment with 5 µg AECHL-1 did not show any change in the normal myocardium, while Paclitaxel, whereas 10 and 20 µg AECHL-1 showed necrosis of myocardial fiber with signs of lymphocytic infiltration. Paclitaxel at 20 µg of dose showed extensive myocardial fiber necrosis with fragmentation and smudging of the myocardium (FIG. 11F-J).

No significant change was observed in kidney structure from AECHL-1 treated group, while paclitaxel treatment showed signs of tubular vacuolization dilation with hemorrhagic areas (FIG. 11K-O).

Liver from Paclitaxel and AECHL-1 treated groups' showed the central vein with portal triads. Both AECHL-1 and Paclitaxel did not show any change in the normal architecture of liver (FIG. 11P-T).

Figure 12:
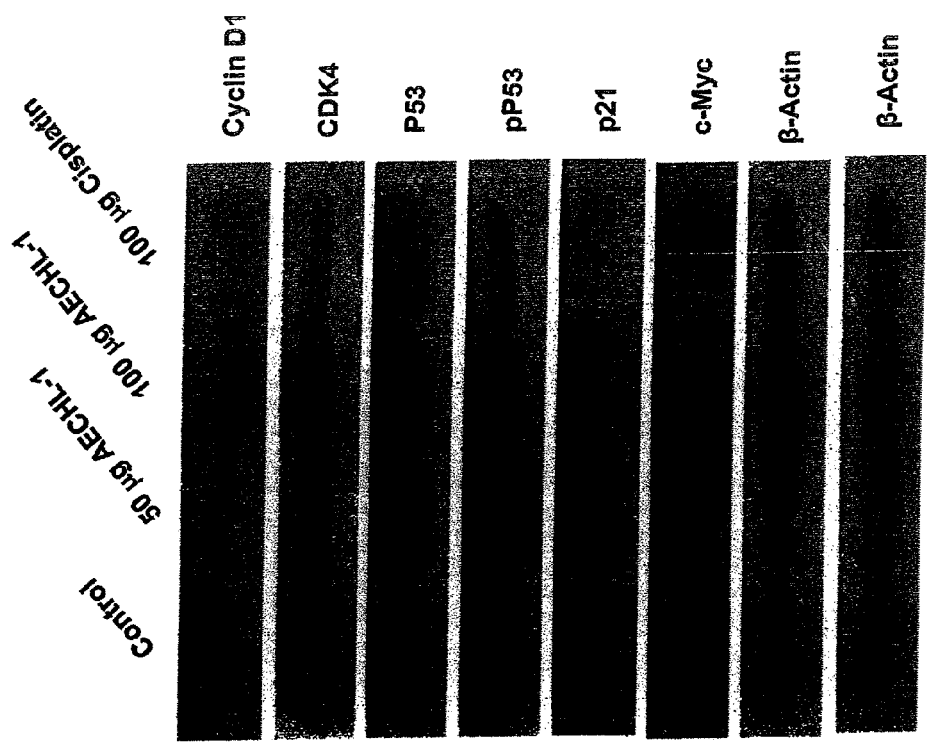

FIG. 12 AECHL-1 induced upregulation in the expression of the checkpoint protein p53 (tumor-suppressor protein), cell arrest protein p21 and downregulation of c-Myc (oncogenic molecules). The p53 protein showed increasing expression at both 50 µg and 100 µg of AECHL-1 as well as in cisplatin compared with control.

DETAILED DESCRIPTION OF INVENTION

Fixation of dose for in vivo studies was done on the basis of in vitro experiments carried out in the present investigation where, no mortality was observed at the selected doses in both C57 and athymic nude mice within 21 days. Intra tumor injection of AECHL-1 for 12 days in C57 mice (at dose level of 50 and 100 µg) and for 10 days in athymic nude mice (at a dose level of 5, 10 and 20 µg) reduced tumor volume significantly compared with control. The results were more significant at lower concentration. Microscopic examination of the tumor in C57 and athymic nude mice showed increased cell density and neovascularization with presence of hemorrhagic areas which showed the probable signs of angiogenesis in control animals, whereas AECHL-1 treated group showed decreased cell density, neovasulization with increased necrotic/apoptotic cells.

Inventors found that the anti-tumor effects of AECHL-1 were comparable with other conventional chemotherapeutic drugs, paclitaxel and cisplatin. Compared with cisplatin, AECHL-1 showed less toxicity in terms of kidney and cardiac damage.

AECHL-1 influences the expression of key molecules that regulate the cell cycle progression i.e. p53, p21, c-Myc, cyclin D1 and Cdk4. Western blot analysis of tumor cells isolated from C57 mice treated with AECHL-1 showed up regulation of p53, p21 levels and down regulation of cyclin D1, CDK4 and oncogenic molecules c-Myc expression, which suggests that down regulation of cyclin D1 and CDK4 expression and up regulation of p53 contributes to the growth inhibition induced by AECHL-1 through a cyclin D1/Cdk4 signaling pathway or from down-regulation of oncogenic molecule c-Myc that help in the tumor growth.

MCF-7 cells after treatment with AECHL-1, showed polymerization of tubulin along with translocation of P53 in the nucleus Which regulate the expression of other signaling molecules that help in the inhibition of cancer cell growth.

Thus AECHL-1 was proved to be an effective new chemical moiety in the treatment of solid tumor. The effect was more pronounced in breast cancer.

Methods

Extraction and Isolation of AECHL-1 from Chloroform Extract of *Ailanthus* Root Bark The chloroform extract (1.5 gm) of powered root bark of *Ailanthus excelsa*, was subjected to column chromatography over silica gel and eluted with chloroform:methanol mixtures. Elutes of 50 ml each were collected and analyzed by thin layer chromatography (TLC). The first few elutes of chloroform consisted of sticky dark brown mass were rejected, while the fraction eluted at, (98:2 v/v) consisted of deep green color fluorescence was further eluted with increasing amount of methanol to remove the fluorescent fraction completely. Elution with further increasing polarity (chloroform:methanol 90:10 v/v) yields light hairy white colored solid mass after concentrating elutes. This mass when subjected to TLC showed three spots which were purified by repeated recrystallization in methanol. After purification it showed single blue colored band at 254 nm which gets pink after treatment with anisaldehyde sulphuric acid reagent after developing in chloroform:methanol (9:1 v/v). This single peak indicated that the preparation was >99% pure. The compound was designated as AECHL-1 (Yield-180 mg). AECHL-1 was characterized by UV, IR, NMR and mass spectroscopy.

Antibodies and Reagents

Rabbit polyclonal anti-p21 and anti-pp53 antibodies were purchased from Santa Cruz Biotechnology (Santa Cruz, Calif.). Mouse monoclonal anti-CDK4 and anti-Cyclin D1 antibodies were from Cell Signaling Technology (Beverly, Mass.). Mouse monoclonal anti-p53 and c-Myc antibodies were from Abcam (USA). Mouse monoclonal anti-actin was from MP Biomedicals (Ohio, USA) and mouse monoclonal anti-tubulin, Cisplatin and Paclitaxel were purchased from Sigma (St. Louis, Mo.). The [$^3$H] Thymidine was purchased from Board of Radiation and Isotope Technology (Mumbai, India). All other chemicals were of analytic grade.

Cell Culture

HEK 293 (Human embryonic kidney cell line), B16F10 mouse melanoma cells, MDA-MB-231 human breast carcinoma, MCF-7 human breast cancer and PC3 human prostate cancer cells were obtained from the American Type Culture Collection (Manassas, Va.). PC3 cells were cultured in Ham's F12 medium (Sigma), HEK 293, MCF-7 and B16F10 cells were cultured in Dulbecco's modified Eagle's medium, (Sigma) and MDA-MB-231 cells were cultured in Leibovitz's L-15 supplemented with 10% FCS (Gibco), 100 units/mL penicillin, 100 µg/mL streptomycin, and 2 mmol/L glutamine in a humidified atmosphere of 5% $CO_2$ and 95% air at 37° C. and MDA-MB-231 cells were cultured in normal humidified atmosphere without $CO_2$ at 37° C.

Cell Viability Assay

The cytotoxic effect of AECHL-1 on the HEK 293, B16F10, PC3, MCF 7 and MDA-MB-231 cells was measured by MTT assay as described in previous studies. The cells were dispensed in 96-well, flat bottom microtiter plates (Becton Dickinson Labware) at a density of $5 \times 10^3$ cells each well. After 24 h, they were treated in 100 µl medium with various concentrations of AECHL-1 (0-150 µM), Cis-platin (0-100 µM) or Paclitaxel (0-50 µM) for 12, 24, and 48 h. MTT [3-(4,5-dimethylthiazol-2yl)-2,5-diphenyl tetrazolium bromide] solution (5 mg/ml in PBS) was added at the end of experiment to each well to a final concentration of 0.5 mg/ml, and the cultures were incubated for further 4 h. The resulting formazan crystals were dissolved in 100 µl dimethylsulfoxide (DMSO) and absorbance was measured in a microplate reader at 570 nm (Molecular Devices, Spectra MAX 250). The cytotoxic effect was expressed as a relative percentage of inhibition calculated as follows:

Relative inhibition(%)=[($A_{570\ control}-A_{570\ AECHL-1}$) $A_{570\ control}$]×100

Cell Proliferation Assay

Aliquots of complete medium containing $5 \times 10^3$ cells (B16F10, PC3, MDA-MB-231 and MCF-7 cells) were distributed into 96-well tissue culture plates. On the following day, the media were replaced with 100 µl of fresh media containing various concentrations of the AECHL-1 (0-150 µM), Cis-platin (0-100 µM) or Paclitaxel (0-50 µM). After 6 h incubation, 1 µCi [$^3$H]thymidine was added to each well. Cells were harvested after 24 and 48 hrs of treatment on a glass filter paper with a 96-well auto-harvester and the amount of incorporated [$^3$H]thymidine was determined with a β-counter (Canberra packard).

Cell Cycle Analysis

The cell cycle analysis of MCF-7, B16F10 MDA-MB-231 and PC3 cells was done by flow cytometry. Cells were plated in 6-well plate ($3 \times 10^5$ cells/well) and treated with various concentrations of AECHL-1 (0-100 µM) and Paclitaxel (0-50 µM) for 24 h. Cells were harvested with trypsin (0.05%), 0.02% EDTA, 0.05% glucose and a single-cell suspension was prepared. Cells were washed and were pelleted by centrifugation (1000×g for 2 min) and fixed in 70% ethanol while vortexing and stored at 4° C. for 1 hour. Fixed cells were pelleted by centrifugation, to remove ethanol and washed with PBS. Cells were re-suspended in PBS containing 50 µg/ml propidium iodide, 0.1 g/L RNase and 1% BSA, incubated for 30 min at 37° C. in the dark, and analyzed with flow cytometry (FACS Vantage-BD Sciences, USA) equipped with an argon laser at 488 nm. The data was analyzed using Cell Quest software for determining the percent population in different phases of cell cycle.

Immunocytochemistry

Immunocytochemistry was performed as described previously. After 24 hour of treatment with AECHL-1 or Paclitaxel, cells were fixed with 3.7% Para-formaldehyde in PBS for 15 minutes, and then permiabilized with 0.1% triton-X100 for 5 minutes and than blocked with 2% BSA and 5% goat serum for 30 minutes. Cells were incubated with primary anti-p53 antibodies (1:100; Abcam) and anti-α-tubulin antibodies (1:10000; Sigma chemical Co.) for 1 hour at room temperature. After washing with PBS, cells were incubated with CY2-conjugated secondary antibodies (1:200; Chemicon, Germany) and Alexa-conjugated secondary antibodies (1:10000; Sigma, St. Louis, Mo.) for 45 minutes and nuclear staining was done with DAPI. Images were captured under confocal microscope.

In Vivo Allograft and Xenograft Tumor Model

Male C57B1/6 mice (6-8 weeks of age) were obtained from National Centre for Cell Science for allograft model, and female athymic nude mice, NTH, nu/nu (Swiss) were obtained from National Institute of Virology (Pune, India) for xenograft model. Male C57B1/6 mice were kept in standard housing with standard rodent chow and water available ad libitum at a 12-hour light/dark cycle while female athymic nude mice were housed under specific pathogen-free conditions and used for in vivo tumorigenicity studies. All procedures were carried out according to specified regulations of the Central Animal Ethical Committee. The animals used were cared for in accordance with the principles of the "guide for care and use of laboratory animals" prepared by the National Academy of Sciences (NIH publication 85-23 revised 1985). Following one week of acclimation, in the allograft model, only a single cell suspension of B16F10 melanoma cells ($5 \times 10^6$/0.1 ml) with >95% viability done using trypan blue exclusion test were injected subcutaneously in the flank of C57B1/6 mice. B16F10 tumors became palpable around 7 days after tumor cell inoculation. In the xenograft model the tumorigenicity experiments were performed as described earlier. Briefly, single cell suspension of MCF-7 ($2 \times 10^7$/0.1 ml) were injected subcutaneously into the flanks of female athymic nude mice. Each mouse was implanted s.c. with a 0.72-mg 17-β-estradiol pellet 2 weeks before inoculation. Animals were assessed for the presence of tumors every alternate day and tumor measurement began 10 days after implantation and continued biweekly until tumors reached approximately 8-10% of animals' body weights. The length (L) and width (W) of tumors were measured using vernier calipers (Mitutoyo, Kawasaki Kanagawa, Japan) and tumor volume calculated using the formula L×W2/2. After two weeks, C57B1/6 mice (n=6) were divided into four groups. Intra-tumor injections were given as follows: control (0.05 ml PBS in 0.5% DMSO), AECHL-1 (50 µg/0.05 ml), AECHL-1 (100 µg/0.05 ml) and cisplatin (100 µg/0.05 ml) for 12 days. Female athymic nude mice (n=3) were divided into five groups and intra-tumor injections were given as: control (0.05 ml PBS in 2% DMSO), AECHL-1 (5 µg/0.05 ml), AECHL-1 (10 µg/0.05 ml), AECHL-1 (20 µg/0.05 ml) and paclitaxel (20 µg/0.05 ml) for 10 days. Tumor volume was measured at regular interval during the study. At the end of the experiment, animals were sacrificed under etheral anesthesia and tumor and other organs like kidney, heart, liver, spleen, and pancreas were dissected out. Half of the tumors and other organs were fixed in 10% buffered formalin and embedded in paraffin for histological analyses by light microscopy. The levels of Cyclin D1, CDK4 p53, pp53, p21 and c-Myc were analyzed by Western blot in tumor homogenates of C57B1/6 mice.

Western Blot Analysis

Prior to immunoblot analysis, tumor segments stored at −80° C. were thawed, washed, minced and homogenized in lysis buffer (120 mM NaCl, 1.0% Triton X 100, 20 mM Tris-HCl, pH 7.5, 10% glycerol, 2 mM EDTA, Protease inhibitor cocktail, Roche) using a Polytron homogenization device. Lysates were incubated at 4° C. for 30 min and centrifuged at 14000 r.p.m. in an Eppendorf micro centrifuge for 15 min. Proteins were isolated in soublised form. Protein concentrations were measured by Bradford assay (Bio-Rad protein assay kit) and stored at −80° C. For immunobloting, 60 µg of total protein from the tumor lysates were used Proteins were resolved in a 10% SDS-polyacrylamide gel, transferred to the immobilon-P nitrocellulose membrane and blocked with 5% (wt/v) non fat dry milk powder (Sigma) in TBST buffer (10 mM Tris pH 7.6, 150 mM NaCl and 0.1% Tween-20) for three hours at room temperature and then incubated with primary antibodies p53, pp53, p21, Cyclin D1, CDK4 and c-Myc in TBST for 3 h and with actin for 1 hour at room temperature. The membrane was incubated further with the secondary antibody HRP-conjugated (BD Bioscience) at 1:10000 dilution for 1 h at room temperature. Following each antibody incubation, the membrane was washed thoroughly with TBST buffer 3 times. The protein bands were visualized using the enhanced chemiluminescence substrate reaction (Pierce) according to the manufacturer's instructions using X-OMAT AR5 film (Kodak)

Statistical Analysis

The data reported for tumor volumes are expressed as mean±SEM. Statistical differences were determined by ANOVA and post test applied was Tukey-Kramer multiple comparison Test. For Tumor to body weight ratio post test applied was Dunnett multiple comparisons test.

Results

HPLC-Analysis of AECHL-1
  Sample: AECHL-1
  Mobile phase: Methanol:Water (90:10)
  Flow rate: 1 ml/min
  UV max: 235 nm
  Concentration: 100 ppm
  Column: RP C-18 Phenomenex column
  Retention Time (RT): 4.734 mins Characterization of AECHL-1

AECHL-1 when subjected to characterization showed following characteristic IR, NMR and mass spectra.

IR (KBr): 3425, 3419 (hydroxyl group), 2972, 2966, 2923, 2873 (alkyl C—H stretch), 1733 (δ lactone), 1718 (Bi acetyl), 1680 (C═O conjugation with alkene), 1652 (—C═C stretching), 1600 (aromatic), 1492, 1454, 1394 (methyl stretching) 1222 (δ lactone), 1184, 1110, 1051, 1031 (acetals), 1018 nm (alkanes).

$^1$H-NMR (DMSO, 400 Hz) δ: 0.95 (3H, t, 4'-CH$_3$), δ: 1.15 (3H, d, H-24), δ: 1.235 (3H, d, 5'-CH$_3$), δ: 1.5 (2H, ddd, 5'-CH$_2$), δ: 1.73 (3H, ddd, H-21), δ: 1.83 (1H, s, H-9), δ: 1.87 (1H, s, H-14), δ: 1.9 (2H, s, H-18), δ: 2.16 (3H, s, H-18), δ: 2.3 (3H, d, H-19) δ: 2.71 (2H, s, H-20), δ: 3.45 (2H, dd, H-23) δ: 3.65 (2H, d, H-22), δ: 3.95 (1H, t, H-12), δ: 4.05 (2H, s, H-22), δ: 5.30 (1H, s, H-15), δ: 5.46 (1H, s, OH-2), δ: 5.73 (1H, d, OH-2'), δ: 6.89 (1H, s H-3), δ: 8.82 (1H, s, OH-11).

Chemical shifts are given in ppm on the δ-scale, s=singlet, d=doublet, t=triplet.

The mass spectra showed the following principal peaks: m/z: 1068 due to dimer formation. The actual [M$^+$] was considered to be 543.8, 463.3 [M-C$_4$H$_1$O$_2$], 461.4 [M-C$_4$H$_2$O$_2$], 459.4 [M-C$_4$H$_4$O$_2$], 361.2 [M-C$_9$H$_{11}$O$_4$]. AECHL-1 is a solid, mp. 248-250° C. possessed a molecular formula of C$_{29}$H$_{36}$O$_{10}$ as indicated by EI and ES mass spectra. The IR spectrum showed the presence of hydroxyl (s) (3425 nm, 3419 nm), δ lactone (1733 nm), and aromatic moiety (1600 nm). The UV spectrum gave a characteristic absorption maximum at 235 nm, indicating the presence of auxochromic groups like hydroxyl and ketone. The $^1$H-NMR spectrum of AECHL-1 revealed the presence of an aromatic proton δ 6.89 and a singlet at δ 5.30 which is characteristic of the ester function at C-15. H-22 appeared as an AB system as a singlet at δ 4.05 and doublet at δ 3.65 and H-12 appeared as a triplet at δ 3.95. The methyl group H-19 on the aromatic ring appeared as singlet at δ 2.3. A doublet at δ 1.235 for six protons is assigned at H-5'. H-4' appeared as a triplet at δ 0.95. The methyl group, H-18 appeared as a singlet at δ 2.16

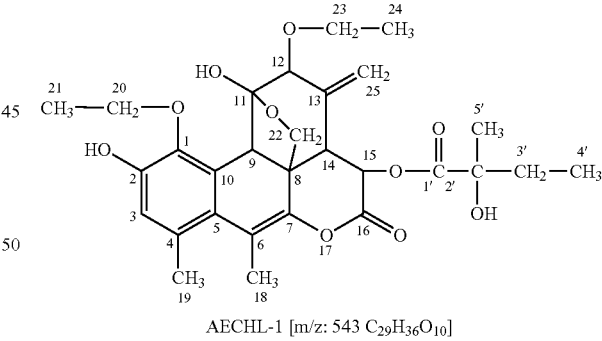

AECHL-1 [m/z: 543 C$_{29}$H$_{36}$O$_{10}$]

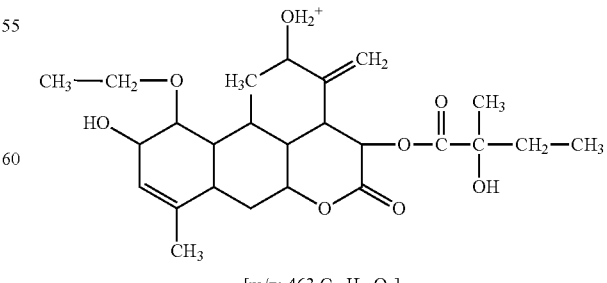

[m/z: 463 C$_{25}$H$_{35}$O$_8$]

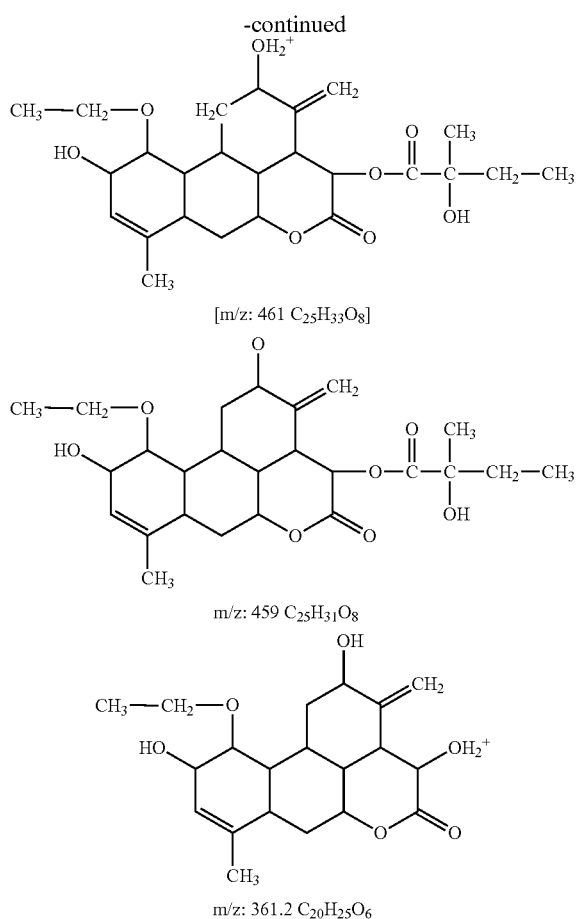

Effect of AECHL-1 on the Proliferation of Tumor Cells In Vitro.

Figure 5:
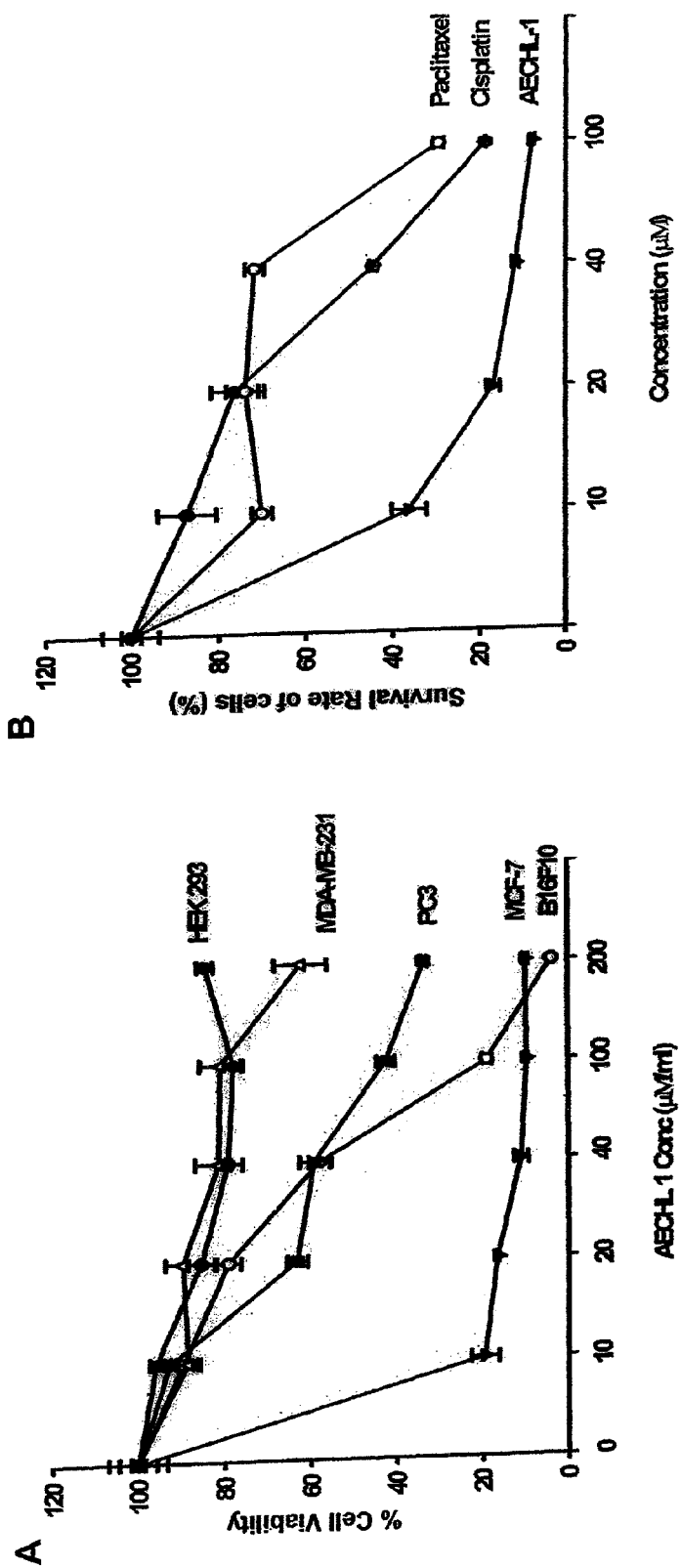
Figure 6:
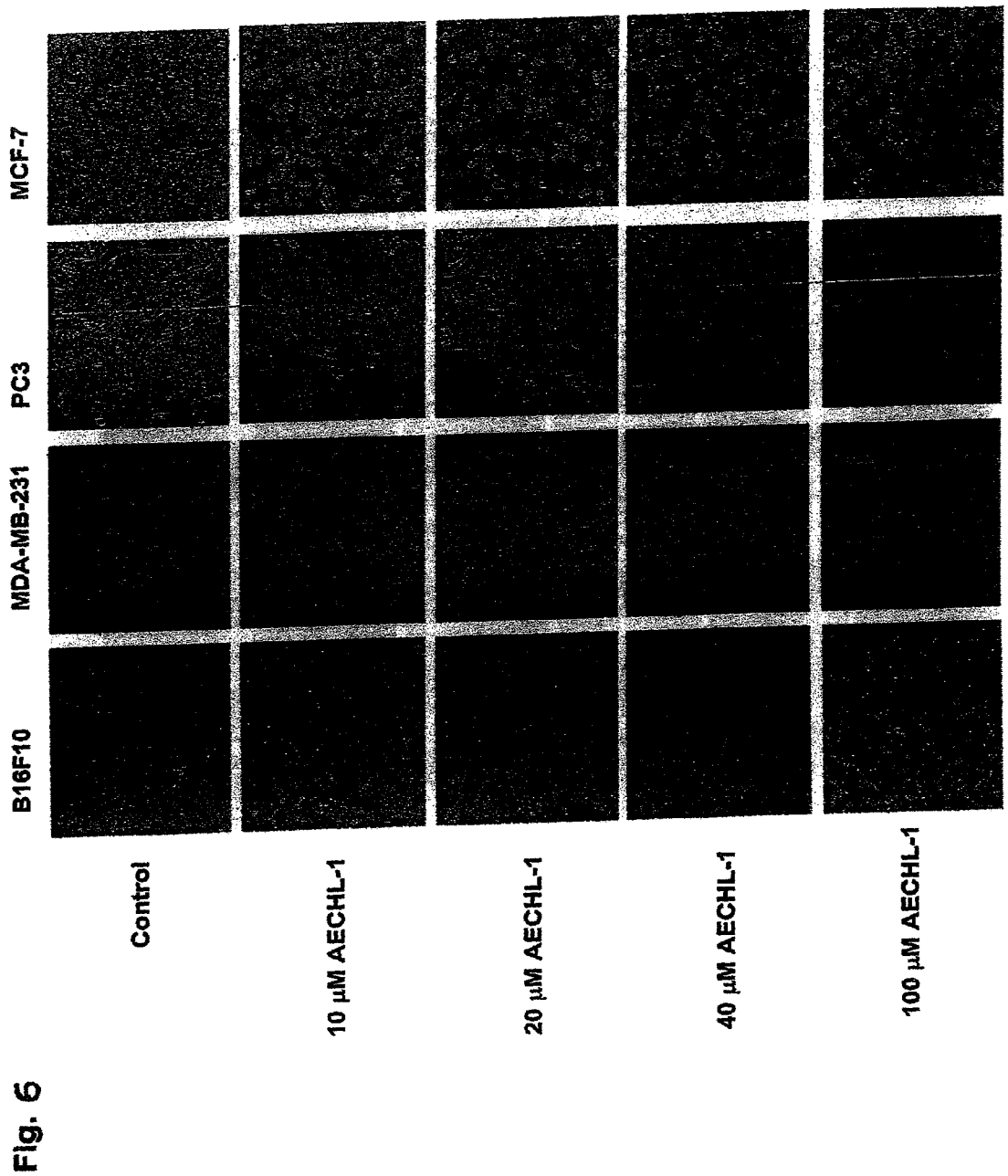

In initial experiments, we examined the effects of different concentration of AECHL-1 on the percent viability and proliferation of tumor cells B16F10, PC3, MDA-MB-231 and MCF-7. As shown in FIG. 5(A-F) after 12, 24 and 48 h of treatment, the percent viability and proliferation of the tumor cells was significantly inhibited by AECHL-1 in a concentration and time dependent manner in all cell lines as indicated by MTT and [$^3$H]thymidine incorporation. The inhibition rate increased in a concentration and time dependent manner, and maximum effect was observed at higher concentration after 48 h of treatment with AECHL-1 in the cell lines as MCF-7>B16F10>PC3>MDA-MB-231>HEK 293 (FIG. 5A).

Significantly, the inhibitory effect of AECHL-1 at 10 μM was stronger than that of Paclitaxel, or Cisplatin in MCF-7 cells treated for 48 h (FIG. 5B) suggesting that AECHL-1 is very potent.

Figure 1:
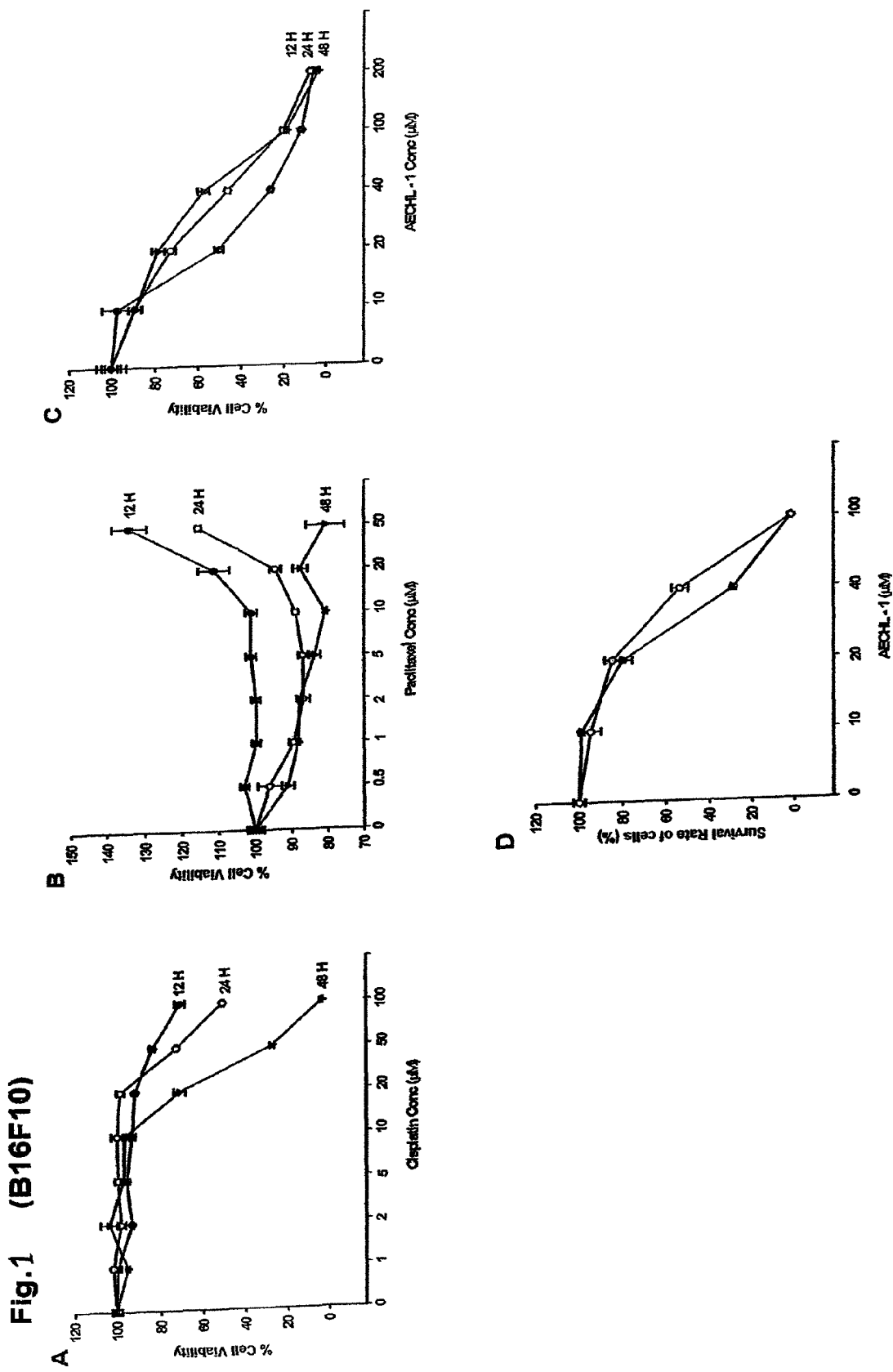
Figure 2:
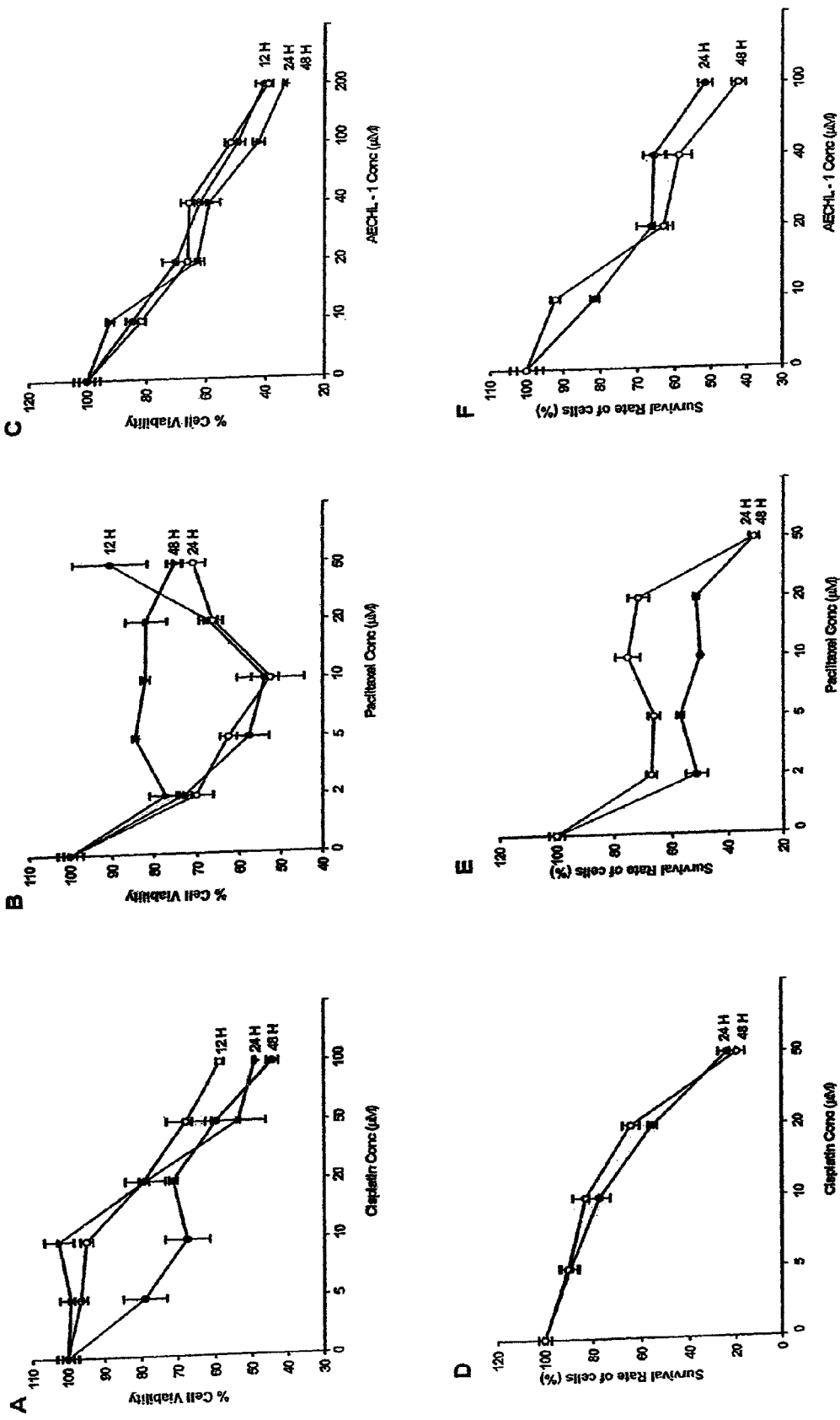
Figure 3:
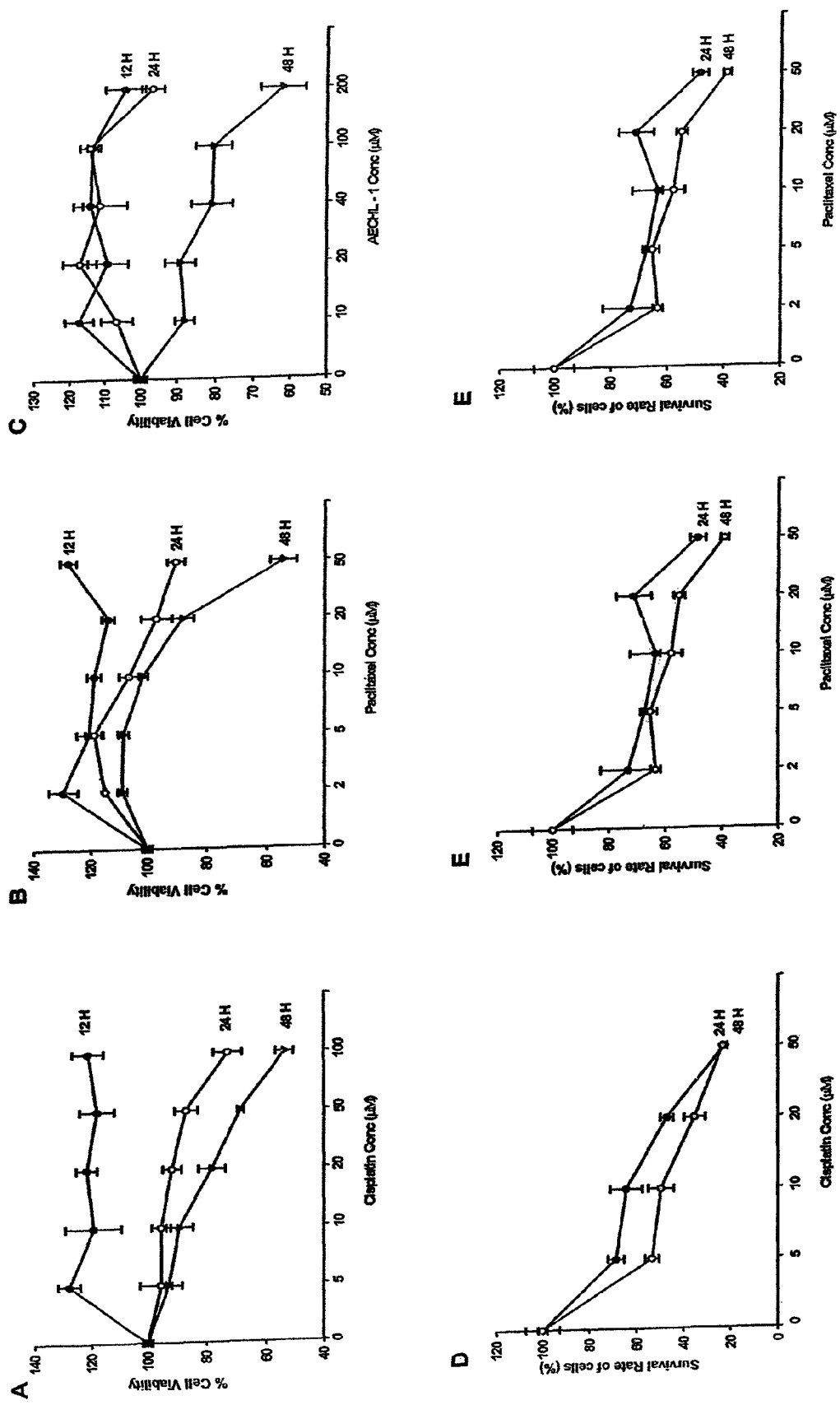
Figure 4:
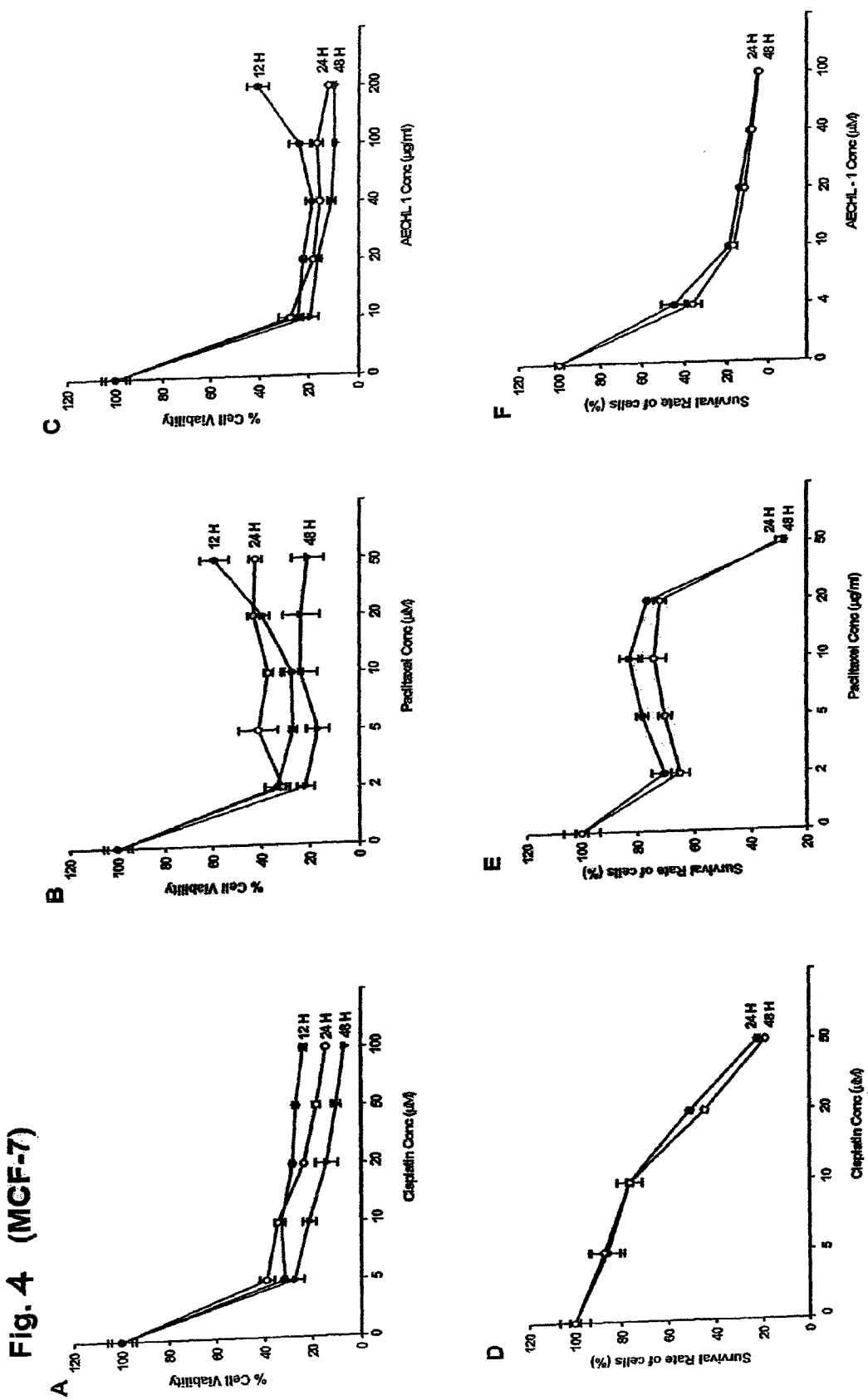

FIG. 4. The relative cell growth arrest of different cells at different concentrations is evident visually in phase contrast images of random fields of cells.

Table 1. Effect of AECHL-1 on Cell Cycle Distribution by Flow Cytometer a) B16F10 cells: In case of B16F10 cells, control cells show a typical pattern of DNA content that reflected G0/G1, S and G2/M phase of the cell cycle. Vehicle treated cells did not showed any significant change in cell distribution pattern, except slight decrease in G0/G1 phase ie 52.18% to that of control 55.64% and increase in G2/M phase cell count ie. 26.59% to that of control cell count 22.98% respectively when compared with control. Treatment with AECHL-1 showed marked increase in G0/G1 cell count ie. 56.55, 57.67, 72.08%, at the concentration of (10, 20, 40, 100 μM) to that of Vehicle control 52.18% respectively. It also showed decrease cell count in S-phase i.e. 20.46, 18.40, 11.43 (for the conc. 10, 20, 40 μM) to that of vehicle control 21.39% respectively. Cell count in G2/M phase was also found to be decreased i.e. 23.02, to 14.73% to that of vehicle treated 26.59% respectively. For the concentration range 10-20 μM of AECHL-1 no apoptotic or necrotic cells were observed. But at higher concentration ie 100 μM cell growths was found to be inhibited due to apoptosis i.e. 7.82% to that of vehicle control 0.24% respectively. At 100 μM, the cell distribution was found to be, like, G0/G1-64.04%, S-15.41% and G2/M phase 13.23% respectively. AECHL-1 showed G0/G1 phase arrest at lower concentration and G0/G1 phase arrest with marked apoptosis at higher concentration.

b) PC3 cells: In case of PC3 cells, control cells showed a typical pattern of DNA content that reflected G0/G1-, S- and G2/M-phase of the cell cycle. Vehicle treatment did not show any significant change in the distribution of the cells in the cycle.

Treatment with AECHL-1 (10 to 100 μM) showed decreased cell count in G0/G1 i.e. 50.74% to 42.92% to that of the vehicle treated cells (52.49%) respectively. The cell growth was found to be arrested in S-G2/M phase exhibited with increase cell count from 45.41% to 53.62% at 100 μM treatment of AECHL-1, and decreased cell count in G0/G1 phase. AECHL-1 arrest the growth of PC3 cells in S-G2/M phase. AECHL-1 also showed apoptotic cell death in PC3 cells.

c) MDA-MB-231 cells: In case of MDA-231 cells, control cells showed a typical pattern of DNA content that reflected G0/G1, S and G2/M phase of the cell cycle. Vehicle treated cells did not show any significant change in cell distribution pattern when compared with control.

Treatment with AECHL-1 (10, 20, 40, 100 μM) showed decreased cell count in G0/G1 phase ie. 43.03, 33.18, 26.66 and 22.82% as compared to that of vehicle control 49.16% respectively. Cell count in S-phase was found to be increased with increasing concentration of AECHL-1 i.e. 24.06, 28.63, 28.12, 30.99% to that of vehicle treated 25.73% respectively. Even AECHL-1 treatment increased the cell count in G2/M phase i.e. 32.21, 38.01, 45.14, 46.17% compared to that of vehicle treatment 24.10% respectively. Thus cells get accumulated in S-G2/M phase. AECHL-1 showed MDA-MB 231 cell growth arrest in S-G2/M phase.

d) MCF-7 cells: In MCF-7 cells, AECHL-1 at 10, 20, 40 and 100 μM of concentration showed 35.04, 27.85, 29.68 and 36.26% of cells in G0/G1 phase to that of control with 53.67%. Thus cell growth was found to be decreased in G0/G1 phase. At the same time cell count in S-G2/M phase was increased from 45.13 to 69.4% respectively at 100 μM concentration of AECHL-1. Thus AECHL-1 arrests the growth in S-G2/M phase.

Effect of AECHL-1 on Cellular p53 Translocation and Microtubules.

Figure 7:
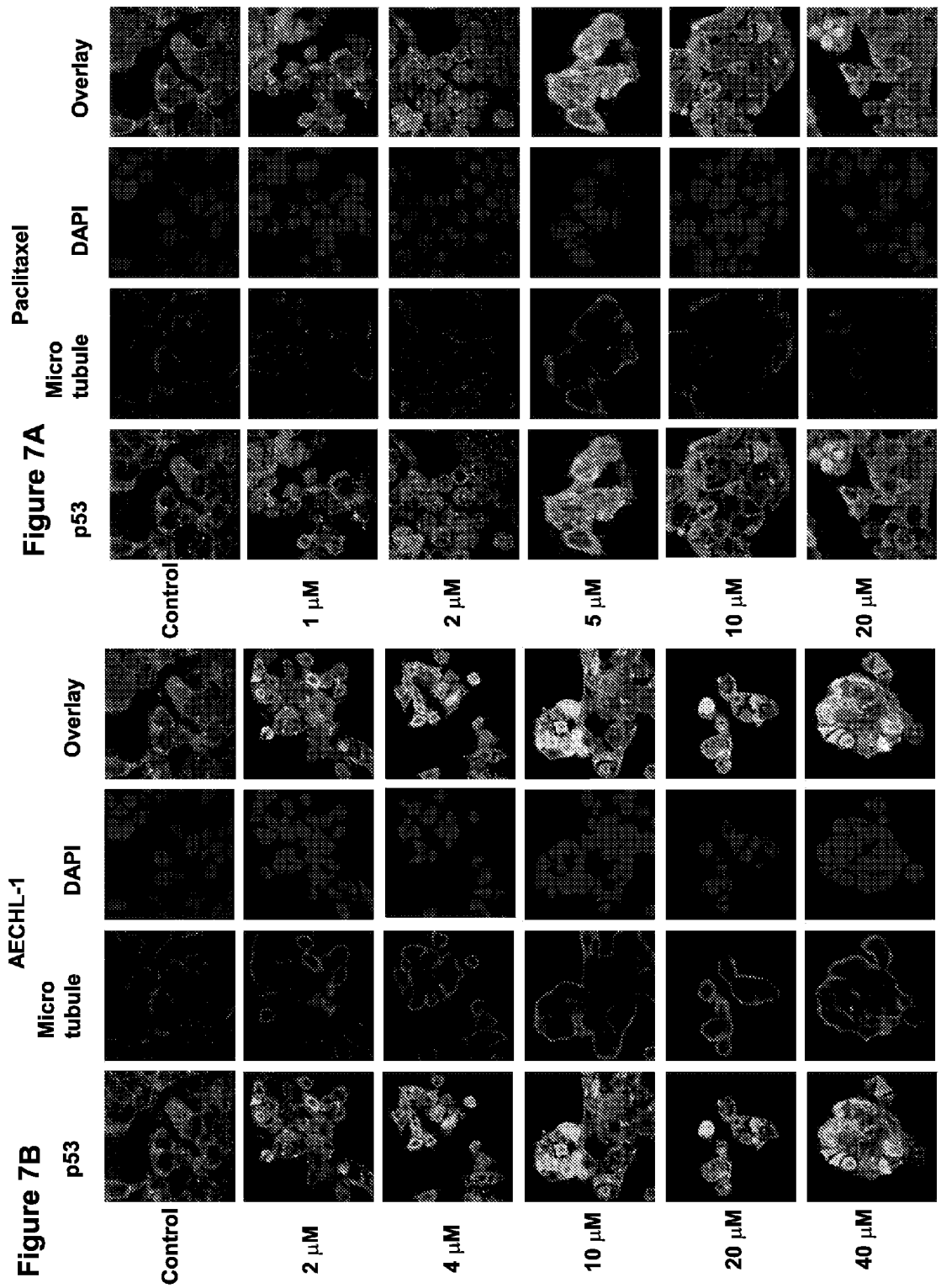

The tumor suppressor p53 plays a critical role in preventing human cancer formation. It translocates into the nucleus and works as a transcription factor by upregulating cell cycle regulatory proteins and induces cell cycle arrest and/or programmed cell death (apoptosis) (11). Therefore, effect of AECHL-1 was studied on the translocation of p53 Also, because paclitaxel exhibits a strong tubulin-stabilizing activity in vitro (12), we tested whether AECHL-1 treatment affected the cellular microtubule network. MCF-7 cells were treated with various concentrations of paclitaxel (1-20 μM)

and AECHL-1 (2-40 μM). After 24 h of incubation, the p53 translocation in the nucleus (green fluorescence) and microtubule network (red fluorescence) was visualized by confocal microscopy. AECHL-1 treatment resulted in translocation of the p53 into the nucleus. The microtubule network in control cells exhibited normal arrangement and organization (FIG. 7). Treatment with paclitaxel resulted in microtubule polymerization with an increase in the density of cellular microtubules and formation of long thick microtubule bundles surrounding the nucleus. AECHL-1 treatment resulted in findings similar to those of paclitaxel-induced microtubule changes, such as thickening and increased density of microtubules.

Effect of AECHL-1 on Primary Tumor Volume in Allograft and Xenograft.

Next, we examined the effects of AECHL-1 on the growth of primary tumor allografts and xenografts of B16F10 cells growing in C57Bl/6 mice and MCF-7 cells growing in athymic nude mice respectively. In preliminary studies, we found that the maximum tolerated dose for AECHL-1 in C57 mice was a single dose of 500 μg/mice and observed for one month and found no obvious sign of toxicity. On this basis, we chose a dose that was 10-20% of this maximum tolerated dose or 50 and 100 μg/kg/day, i.p. or the doses which induced maximum cell death in vitro. This regimen did not appear to adversely affect the mice, because there were no obvious signs of sickness after 2 weeks, and there was no difference in the body weights between groups treated with AECHL-1 and the controls (data not shown). On day $18^{th}$ significant increase in tumor volume was observed in control group (p<0.001). 50 and 100 μg AECHL-1 was administered to these mice with established tumor allografts, the tumor size was reduced by [44.303±5.20% for 50 μg (p<0.001) and 51.014±1.27% for 100 μg (p<0.001) AECHL-1), whereas those that were treated with 100 μg cis-platin showed a reduction of [93.13±0.539% (p<0.001)]. AECHL-1 (50 μg) vs. AECHL-1 (100 μg) was found to be non Significant (P>0.05).

On day $24^{th}$ tumor volume in control AECHL-1 (50 μg) and AECHL-1 (100 μg) was found to be increased (p<0.001), while that in cis-platin treated group volume was found to be decreased (p<0.001).

Although cis-platin was found to be extremely significant than either 50 μg or 100 μg AECHL-1 damage to the other organs in cis-platin treated group was more than in the AECHL-1 treated group (FIGS. 8A and B).

Since the cytotoxic doses of AECHL-1 for MCF-7 cells were very low, the doses selected for tumor xenografts in athymic nude mice were 5, 10 and 20 μg/0.05 ml. At these doses of AECHL-1 the tumor size was reduced by [35.72±0.05% for 5 μg (p<0.001), 28.55±0.06% for 10 μg (p<0.001), 4.1±0.27% for 20 μg (p<0.05) whereas those that were treated with and 20 μg paclitaxel showed a reduction of [14.19±0.32% (p<0.05)], which was less than the AECHL-1 group (FIGS. 8C and D).

These results demonstrated that the anti-tumor effect of AECHL-1 was comparable with or even superior to the conventional chemotherapeutic drugs tested. Thus AECHL-1 at both the concentrations prevents the growth of tumor cells with reduction in tumor volume when compared with control group.

Effect of AECHL-1 on Body Weight and Tumor Weight/Body Weight Ratio

In control group and in mice treated with 100 μg AECHL-1 and Cis-platin, a reduction in body weight (including tumor) was observed. Whereas the body weight was not reduced in case of mice treated with 50 μg AECHL-1 (FIG. 9A).

Treatment with 50 and 100 μg AECHL-1 and cis-platin showed significant reduction in tumor weight to body weight ratio after 12 days treatment (p<0.01) compared with control group. Compared to 100 μg AECHL-1, the effect was more in 50 μg AECHL-1. Compared with AECHL-1 and control groups cis-platin treated group showed significant reduction in ratio (FIG. 7B).

Histological Examination of Tumor Tissue in C57 Mice

When angiogenesis is induced, metastatic tumor cells grow rapidly. Therefore, inhibition of angiogenesis prevents tumor growth, proliferation, and secondary metastasis. Inhibition of angiogenesis and suppression of invasion, motion and proliferation of tumors, and growth of endothelial cells of blood vessel, are essentially required for cancer prevention.

Histological examination of tumor tissue were evaluated for tumor cell density, location, number, and structure of blood vessels to assess possible changes related to angiogenesis; the presence of hemorrhagic areas to determine the vascular integrity of capillaries; and the presence, size, and location of picnotic/necrotic cell areas to investigate tumor viability.

Tumors from vehicle treated group showed increased neovascularization with increased cell density and presence of hemorrhagic areas which showed probable signs of angiogenesis with increased threat of metastasis. The blood vessels were found to be well developed (FIG. 10A). Treatment of tumors with 50 μg AECHL-1 did not show much influence on the tumor vascularization with less occurrence of hemorrhagic areas. Tumor cell density was found to be decreased with occurrence of picnotic/necrotic cells in the center of the tumor. We did not directly assess the functionality of blood vessels in this area, as vessels seemed perfused as indicated by the presence of erythrocytes. Therefore, necrosis in these areas did not seem to be the result of lack of vascularization (FIG. 10B).

Treatment of tumors with 100 μg AECHL-1 showed increase in necrotic nuclei through out the tumor area, with disappearance of neovasulization and hemorrhagic areas and therefore reduced the chances of angiogenesis and metastasis. Tumor cell density was found to be lower compared to that of 50 μg AECHL-1 and vehicle treated group (FIG. 10C).

Cis-platin treated group showed significant increase in necrotic nuclei with decreased tumor cell density (FIG. 10D). Tumor volume was also found to be reduced. There was no sign of neovasulization and hemorrhagic areas. Most of the cells were found to be dead when compared with control and 50 μg AECHL-1.

Thus, AECHL-1 prevents the progression of angiogenesis by blocking neovasulization, thus reducing the risk of metastasis.

Histopathological Examination of Organs in C57 Mice

Histological examination of the organs from C57 mice showed following data Liver from control group showed the central vein with portal triads at the periphery of the lobule. Kupffer cells appeared were normal (FIG. 10E). 50 μg AECHL-1 did not affect the normal architect of the liver (FIG. 10F) and 100 μg AECHL-1 retains the normal architect of the liver with hypertrophic cell nucleus (FIG. 10G). In cis-platin treated group, extensive hepatocytes necrosis was seen. The hepatocytes shown with arrow at the right side are dead. This pattern can be seen with a variety of hepatotoxins, where focal hepatocytes necrosis with lymphocytic infiltration occurs. Histopathologically, lesions look like that of Tyzzer's disease characterised by necrosis with varying degrees of inflammation in response to the necrosis. Acute hepatic lesions consist of necrotic foci urrounded by minimal, primarily neutrophilic, inflammation (FIG. 10H).

Heart from control group showed parallel fibers with prominent centrally placed nuclei indicating individual cells (FIG. 10I). Treatment with 50 µg AECHL-1 did not show any necrosis of myocardial fibers (FIG. 10J). Treatment with 100 µg AECHL-1 showed extensive myocardial fiber necrosis with contraction bands and loss of nuclei. The fragmentation and smudging of the muscle fibers occur which is characteristic of coagulative necrosis (FIG. 10K). Cis-platin treated mice showed necrosis of myocardial fiber occurs with slight lymphocytic infiltration. Here again the fragmentation and smudging of the muscle fibers characteristic of coagulative necrosis (FIG. 10L).

In control mice kidney showed well demarcated cortex and medulla, and the intact capsule with well formed glomeruli (FIG. 10M). Treatment with 50 µg AECHL-1 showed slight tubular vacuolization and tubular dilation with hemorrhagic areas, normal glomeruli appears at the lower part (FIG. 10N). Treatment with 100 µg AECHL-1 showed tubular vacuolization and tubular dilation with hemorrhagic condition, tubules were dilated with scattered chronic inflammatory cell infiltrates (FIG. 10O). In Cisplatin treated mice lymphocytes were scattered in and around the vessel. The glomerulus is hypercellular and capillary loops were poorly defined which is a type of proliferative glomerulo nephritis. Many neutrophils were seen in the tubules and interstitium i.e. Pyelonephritis (FIG. 10P).

No significant changes occurred in the cellular architecture of pancreas histology (FIG. 10Q-T).

Representative spleen sections from control mice showed different compartments of the white pulp indicated by (*)-periarteriolar lymphatic sheaths; (Θ)-follicles; and (Ψ)-marginal zones. Control and 50 µg AECHL-1 showed normal spleen architect Note the hyperplasia of the white pulp, especially of the follicles; and marginal zone. Histology showed increased number of granulocytes in the marginal zones (FIG. 10U-X).

Histological Examination of Tumor Tissue in Nude Mice

Histological examination of tumor in nude mice were similar to that of C57 mice. Tumors from control mice showed pronounced neovascularization throughout the section surrounded with highly dense cells and absence of necrotic cells (FIG. 11A). Treatment with Paclitaxel lowered the tumor cell density with occurrence of many empty spaces and necrotic areas in the section. Paclitaxel did not influence the tumor vascularization with occurrence of blood vessels and hemorrhagic areas (FIG. 11B). AECHL-1 at 5 µg dose showed decreased tumor cell density with lots of empty spaces throughout the tumor area. It also showed loss of neovasulization with absence of hemorrhagic areas (FIG. 11C). AECHL-1 at 10 and 20 µg showed similar effects, but was not able to reduce the vasculization with occurrence of hemorrhagic areas. We did not directly assess the functionality of blood vessels in this area, as vessels seemed perfused as indicated by the presence of erythrocytes. Therefore, necrosis in these areas did not seem to be the result of lack of vascularization (FIGS. 11D and E).

Histopathological Examination of the Organs in Nude Mice

Treatment with 5 µg AECHL-1 did not show any change in the normal myocardium, while Paclitaxel, whereas 10 and 20 µg AECHL-1 showed necrosis of myocardial fiber with signs of lymphocytic infiltration. Paclitaxel at 20 µg of dose showed extensive myocardial fiber necrosis with fragmentation and smudging of the myocardium (FIG. 11F-J).

No significant change was observed in kidney structure from AECHL-1 treated group, while paclitaxel treatment showed signs of tubular vacuolization dilation with hemorrhagic areas (FIG. 11K-O).

Liver from Paclitaxel and AECHL-1 treated groups' showed the central vein with portal triads. Both AECHL-1 and Paclitaxel did not show any change in the normal architecture of liver (FIG. 11P-T).

Tumor Cell Growth Arrest Associated With Protein Expression

Figure 9:
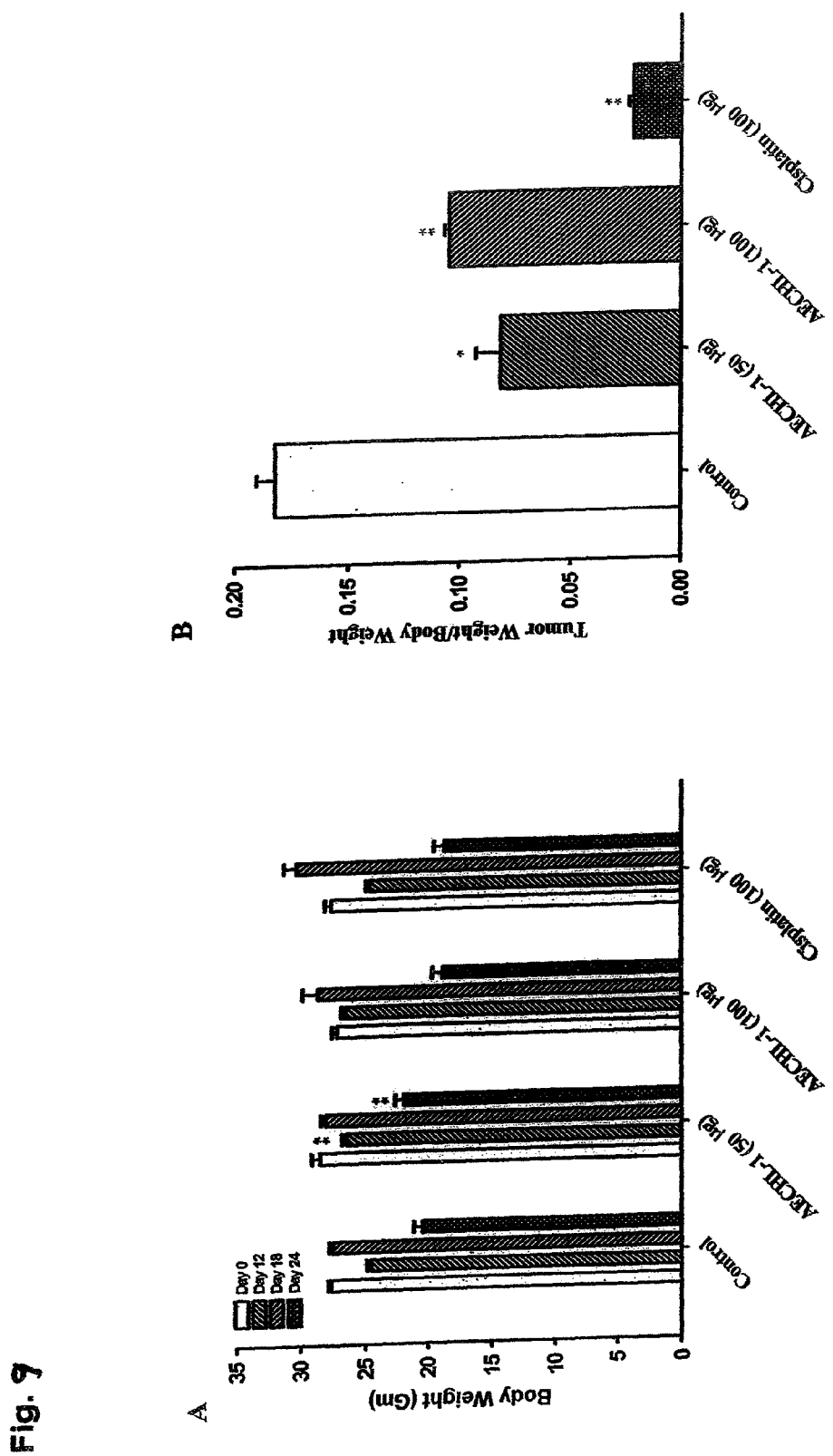

Because AECHL-1 showed growth arrest in all cell types, we next tested for molecules that control cell cycle. The results of Western blots revealed that AECHL-1 reduced the expression of cyclin D1 and CDK4. AECHL-1 induced upregulation in the expression of the checkpoint protein p53 (tumor-suppressor protein), cell arrest protein p21 and downragulation of c-Myc (oncogenic molecules). The p53 protein showed increasing expression at both 50 µg and 100 µg of AECHL-1 as well as in cisplatin compared with control (FIG. 9). However, the expression was less in 100 µg compared to expression at 50 µg of AECHL-1. The phosphorylation of p53 (pp53) protein increasing at 50 µg and then decreased at the 100 µg concentration of AECHL-1. Whereas, cisplatin did not show any change. There was a decrease in the expression of p21 at 50 µg and then increased at the 100 µg concentration of AECHL-1. Cisplatin showed increased p21 expression. This suggests that down regulation of cyclin D1 and CDK4 expression and up regulation of p53 contributes to the growth inhibition induced by AECHL-1 through a cyclin D1/Cdk4 signaling pathway or from down-regulation of oncogenic molecule c-Myc that help in the tumor growth.

TABLE 1

Cell cycle analysis of AECHL-1-treated cells

| Cell line | Compound | Conc (µM) | Sub $G_0$ | $G_1$ | S | $G_2$/M |
|---|---|---|---|---|---|---|
| B16F10 | AECHL-1 | 0 | 0.24 | 52.18 | 21.39 | 26.59 |
| | | 10 | 0.39 | 56.55 | 20.46 | 23.02 |
| | | 20 | 0.65 | 57.67 | 18.40 | 23.60 |
| | | 40 | 2.05 | 72.08 | 11.43 | 14.73 |
| | | 100 | 7.82 | 64.04 | 15.41 | 13.23 |
| PC3 | AECHL-1 | 0 | 1.44 | 52.49 | 16.21 | 29.70 |
| | | 10 | 1.66 | 50.74 | 16.21 | 30.94 |
| | | 20 | 1.79 | 48.96 | 13.99 | 34.99 |
| | | 40 | 4.14 | 44.26 | 17.71 | 33.82 |
| | | 100 | 3.36 | 42.92 | 18.25 | 35.37 |
| MDA-231 | AECHL-1 | 0 | 1.48 | 49.54 | 25.79 | 23.61 |
| | | 10 | 1.03 | 43.03 | 24.06 | 32.21 |
| | | 20 | 0.95 | 33.18 | 28.63 | 38.01 |
| | | 40 | 0.54 | 26.66 | 28.12 | 45.15 |
| | | 100 | 0.58 | 22.82 | 30.99 | 46.17 |
| MCF-7 | AECHL-1 | 0 | 1.64 | 53.67 | 19.03 | 26.10 |
| | | 4 | 1.61 | 35.04 | 27.20 | 36.65 |
| | | 10 | 1.99 | 27.85 | 34.19 | 36.78 |
| | | 20 | 1.81 | 29.68 | 37.44 | 31.98 |
| | | 40 | 2.55 | 36.26 | 32.50 | 29.42 |
| MCF-7 | Paclitaxel | 0 | 3.17 | 48.30 | 20.42 | 29.30 |
| | | 1 | 3.45 | 4.62 | 18.65 | 72.55 |
| | | 2 | 5.21 | 7.41 | 22.89 | 63.71 |
| | | 5 | 3.98 | 5.34 | 18.35 | 72.86 |
| | | 10 | 3.47 | 4.86 | 18.96 | 69.36 |

We claim:

1. An isolated triterpenoid having the following characteristic NMR:

$^1$H-NMR (DMSO, 400 Hz) δ: 0.95 (3H, t, 4"-CH$_3$), δ: 1.15 (3H, d, H-24), δ: 1.235 (3H, d, 5'-CH$_3$), δ: 1.5 (2H, ddd, 5'-CH$_2$), δ: 1.73 (3H, ddd, H-21), δ: 1.83 (1H, s, H9), δ: 1.87 (1H, s, H-14), δ: 1.9 (2H, s, H-18), δ 2.16 (3H, s, H-18), δ: 2.3 (3H, d, H-19) δ: 2.71 (2H, s, H-20), δ: 3.45 (2H, dd, H-23), δ: 3.65 (2H, d, H-22), δ: 3.95 (1H, t, H-12), δ: 4.05 (2H, s, H-22), δ: 5.30 (1H, s, H-15), δ: 5.46 (1H, s, OH-2), δ: 5.73 (1H, d, OH-2'), δ: 6.89 (1H, s, H-3) δ: 8.82 (1H, s, OH-11); having a melting point of 248-250° C. and having the structure:
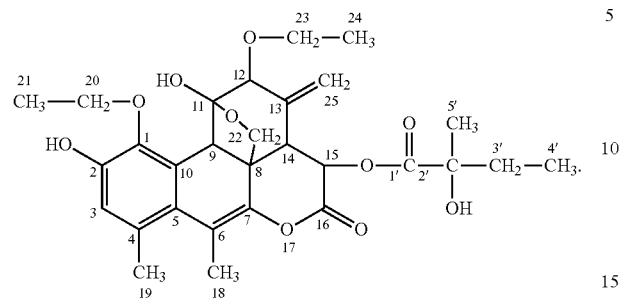
* * * * *

UNITED STATES PATENT AND TRADEMARK OFFICE
CERTIFICATE OF CORRECTION

PATENT NO. : 8,519,163 B2  
APPLICATION NO. : 12/742139  
DATED : August 27, 2013  
INVENTOR(S) : Sitasawad et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 10 days.

Signed and Sealed this
Fifteenth Day of September, 2015

Michelle K. Lee
*Director of the United States Patent and Trademark Office*